United States Patent [19]

Karger et al.

[11] Patent Number: 4,898,658
[45] Date of Patent: Feb. 6, 1990

[54] INTEGRATED TEMPERATURE CONTROL/ALIGNMENT SYSTEM FOR HIGH PERFORMANCE CAPILLARY ELECTROPHORETIC APPARATUS

[75] Inventors: Barry L. Karger, Newton; Aran Paulus, Boston; Aharon S. Cohen, Brookline; Robert J. Nelson, Boston, all of Mass.

[73] Assignee: Northeastern University, Boston, Mass.

[21] Appl. No.: 125,539

[22] Filed: Nov. 25, 1987

[51] Int. Cl.$^4$ ............................................. G01N 27/26
[52] U.S. Cl. .............................. 204/299 R; 204/180.1; 204/182.8; 204/183.3
[58] Field of Search .............. 204/299 R, 180.1, 183.3

[56] References Cited

U.S. PATENT DOCUMENTS

| | | | |
|---|---|---|---|
| 3,677,930 | 7/1972 | Meshbane et al. | 204/182.7 X |
| 3,948,753 | 4/1976 | Arlinger | 204/299 R |
| 4,624,768 | 11/1986 | Yoshida et al. | 204/299 R |
| 4,675,300 | 6/1987 | Zare et al. | 204/180.1 X |

FOREIGN PATENT DOCUMENTS

| | | | |
|---|---|---|---|
| 241940 | 10/1987 | European Pat. Off. | 204/299 R |
| 533893 | 1/1978 | Japan | 204/299 R |

Primary Examiner—John F. Niebling
Assistant Examiner—John S. Starsiak, Jr.
Attorney, Agent, or Firm—Weingarten, Schurgin, Gagnebin & Hayes

[57] ABSTRACT

An integrated temperature control/alignment system for use with a high performance capillary electrophoretic apparatus is disclosed. In one exemplary embodiment the integrated temperature control/alignment system comprises a pair of capillary column mounting plates for mounting a capillary column as a constituent of the electrophoretic apparatus, a pair of secondary support plates, a pair of thermoelectric plates and external heat sink plates. Detection openings are formed in each of the plates as required so that a continuous detection path exists through the integrated temperature control/alignment system. The capillary column is seated and locked in grooves formed in the capillary column mounting plates so that the detection windows of the capillary column are coordinated with the aligned detection openings formed in the applicable plates of the integrated temperature control/alignment system. The temperature of substantially the entire capillary column, including the detection zone, is controlled or regulated by the temperatures of the thermoelectric plates which comprise one or more thermoelectric circuits utilizing the Peltier effect. Regulation of current flow in the thermoelectric plates controls the temperature effect exerted by the thermoelectric plates, thereby controlling both the direction and rate of heat transfer with the capillary column.

19 Claims, 3 Drawing Sheets

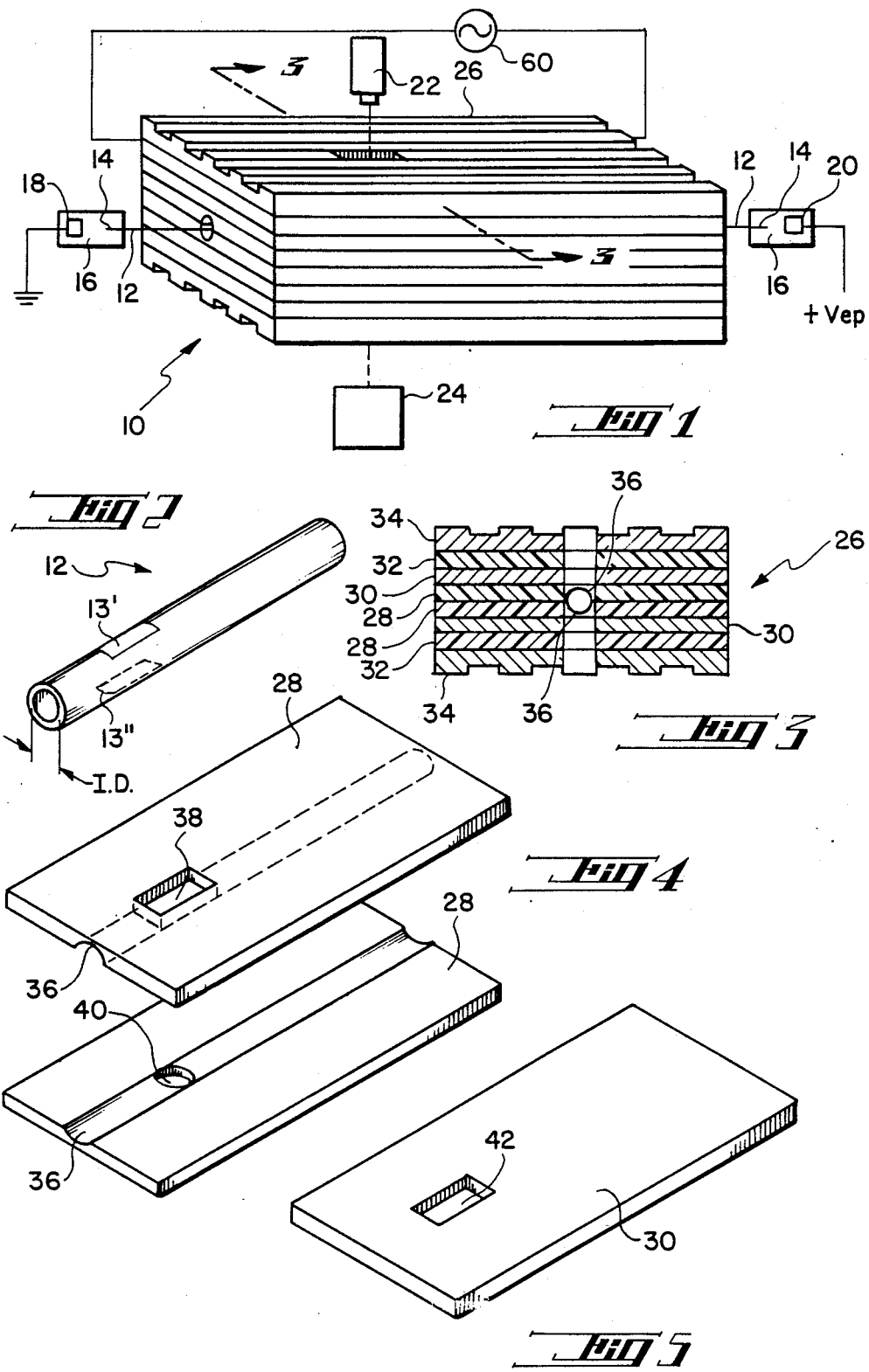

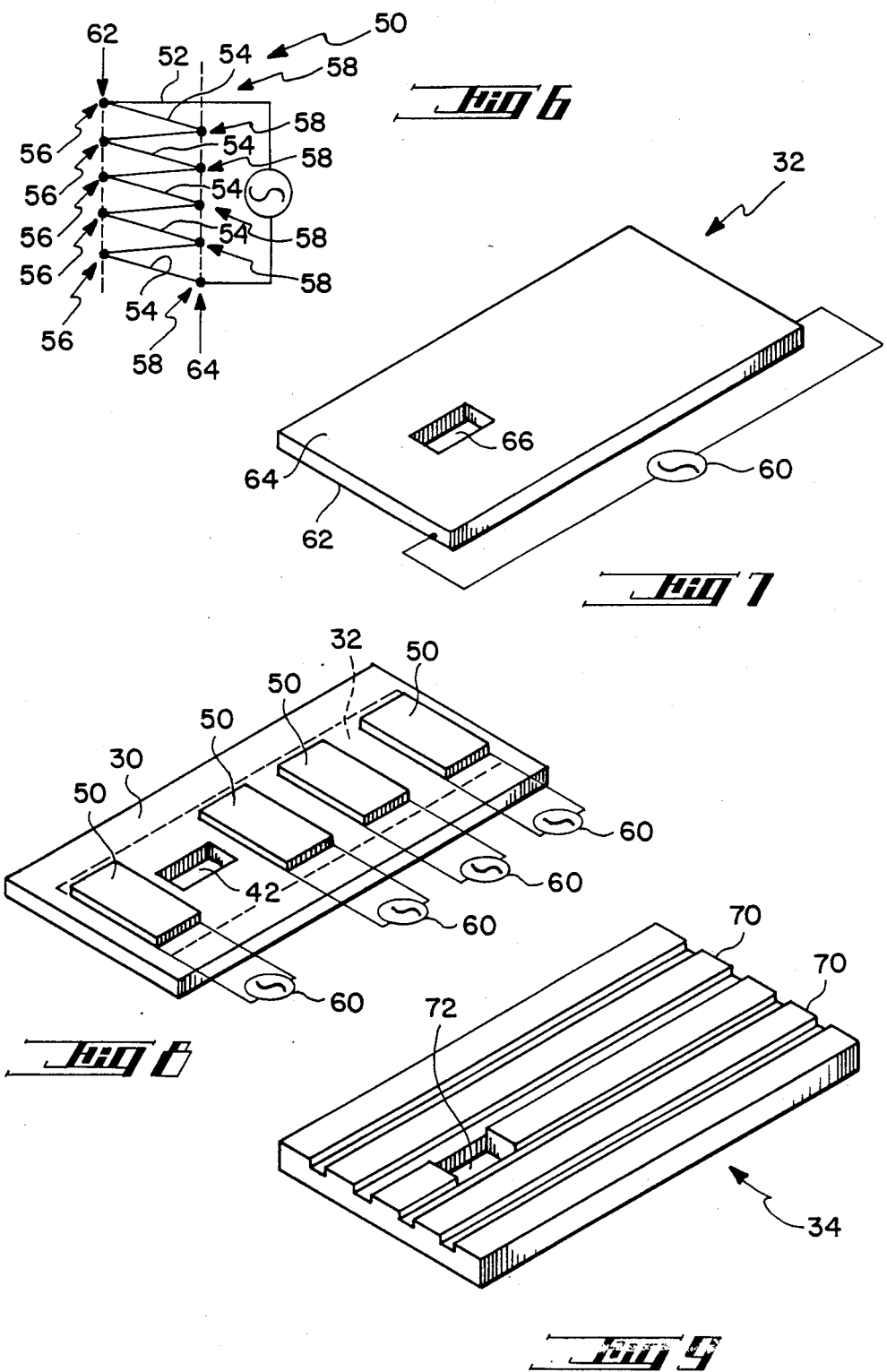

INTEGRATED TEMPERATURE CONTROL/ALIGNMENT SYSTEM FOR HIGH PERFORMANCE CAPILLARY ELECTROPHORETIC APPARATUS

FIELD OF THE INVENTION

This invention relates generally to electrophoretic apparatus, and more particularly to a temperature control/alignment system integrated with a high performance capillary electrophoretic apparatus.

BACKGROUND OF THE INVENTION

Capillary electrophoresis is a technique for analyzing and/or purifying a wide variety of biochemical substances or analytes such as proteins, nucleic acids, carbohydrates, hormones and vitamins. In particular, electrophoresis is an extremely efficacious and powerful means for the identification and/or separation of analytes based upon ultra-small volume samples. In general, electrophoresis is a phenomenon that involves the migration of charged particles or analytes through a conducting liquid solution under the influence of an applied voltage.

The basic capillary electrophoretic apparatus consists of a capillary column having the ends thereof positioned in reservoirs containing electrodes. A conducting liquid or buffer solution disposed in the reservoirs and the capillary column comprises the electrophoretic conductive circuit.

An analyte is injected into the appropriate end of the capillary column and a voltage applied across the electrodes. The applied voltage causes the analyte to migrate electrophoretically through the capillary column past a prepositioned on-column detection device to generate an electropherogram, a graphical representation of the analyte.

Electrophoresis may be conducted in "open" or "gel" capillary columns. Open capillary electrophoresis can be conducted either with or without electroosmosis which involves bulk solvent migration under the influence of the applied voltage as a result of the charged condition of the inner wall of the capillary column. Gel capillary electrophoresis, in which the interior channel of the capillary column is filled with a suitable gel, provides the potential for different modes of separation based upon size of the analytes.

In either open or gel capillary electrophoresis, however, the applied voltage is a primary factor affecting the migration of the analyte. Therefore, the term electromigration as used herein encompasses either or both forms of voltage induced analyte movement.

An effective high performance capillary electrophoretic system provides high resolution, high sensitivity, short run times, on-line monitoring or detection of the analyte, and reproducible performance. One practical way of enhancing the performance of a capillary electrophoretic apparatus is by the application of high applied voltages. Another is to utilize shortened capillary columns. Both of these means of enhancing the effectiveness of the electrophoretic apparatus, however, have heretofore been limited due to the Joule heat generated in the capillary column during the electrokinetic separation operation which adversely affects electrophoretic separations.

The applied voltage causes a current flow in the buffer solution of the electrophoretic apparatus. The current flow through the capillary column generates Joule heat or thermal energy in the capillary column. Increasing the applied voltage increases the current flow which increases the amount of Joule heat generated, which is generally an adverse condition since most electrophoresis is optimally conducted at low, constant temperatures. Similarly, shortening the length of the capillary column decreases the capillary column resistance, thereby causing an increase in current flow for a given applied voltage with the concomitant increase in Joule heating.

An optimized capillary electrophoretic apparatus provides statistically reproducible results for equivalent analytes, with minimum band broadening of the output. Preferably, the apparatus is operated at high applied voltages to provide high speed, efficiency and resolution of separations.

Prior art attempts t cool capillary electrophoretic apparatus have typically involved the use of water as the cooling element. In additional to being high capacity devices, requiring two to four liters of water, water-cooled devices suffered a marked degradation in cooling performance, about 20 to 40 percent, at temperatures approaching four degrees centigrade. Another limiting aspect of prior art capillary electrophoretic apparatus was due to the fact that the structural configuration of prior art temperature regulating systems severely hindered temperature control in the detection zone. A lack of temperature control can lead to non-reproducible results in migration rates and separation.

Moreover, reproducible results in signal-to-noise ratio were difficult to achieve in prior art capillary electrophoretic apparatus due to the cumbersome and time consuming effort required to properly align and lock the capillary column with respect to the prepositioned detection device. Improper alignment of or failure to lock the capillary column in a predetermined position leads to the generation of variable noise due to vibration effects, which can lead to poor detection limits.

SUMMARY OF THE INVENTION

The present invention surmounts the inherent disadvantages of the prior art by providing an integrated temperature control/alignment system for a high performance capillary electrophoretic apparatus. The integrated temperature control/alignment system provides a means for regulating the temperature of the capillary column to a predetermined operating temperature by dissipating or in some instances augmenting, in order to operate at elevated column temperatures, the Joule heat generated by current flow through the capillary column.

Temperature regulation of the capillary column is effected by controlling a secondary current flow through a thermoelectric device, thereby permitting regulating heat transfer away from or into the capillary column. An effective means of temperature regulation permits a higher voltage to be applied across the capillary column than if the system were not present, with the accompanying increase in apparatus performance. The structural configuration of the integrated temperature control/alignment system also permits thermoelectric temperature regulation over the on-column detection zone of the capillary column.

In addition, the integrated temperature control/alignment system provides a means for mounting the capillary column as a constituent of the electrophoretic apparatus. The structural configuration of the integrated temperature control/alignment system facilitates the precise alignment of the detection "windows" of the capillary column with the detection openings of the integrated temperature control/alignment system for on-column detection. The structural configuration of the integrated temperature control/alignment system coacts with the capillary column to lock the capillary column therein in a predetermined aligned position with respect to the on-column detection device. The locking feature of the present invention effectively eliminates adverse vibratory effects which would have affected the output while the alignment feature ensures reproducible results.

One exemplary embodiment of the integrated temperature control/alignment system according to the present invention comprises a pair of capillary column mounting plates for mounting the capillary column as a constituent of the electrophoretic apparatus, a pair of secondary support plates, a pair of thermoelectric plates and external heat sink plates.

The capillary column mounting plates are formed from an electrically insulating material and each plate has a lengthwise groove sized to snugly seat the capillary column. With the capillary column mounting plates disposed in contacting relation with the capillary column sandwiched therebetween in the grooves, the capillary column is effectively locked into position within the integrated temperature control/alignment system.

A detection slit and a detection hole are formed through the respective capillary column mounting plates so as to be substantially centered about the lengthwise groove thereof. The capillary column is seated within the grooves of the capillary column mounting plates so that the detection windows thereof are precisely aligned with the detection slit and hole, respectively. This ensures that the capillary column is mounted as a constituent of the electrophoretic apparatus in alignment with the prepositioned on-column detection device.

The secondary support plates are fabricated and utilized to facilitate heat transfer between the encapsulated capillary column and the thermoelectric plates as well as to provide for increased structural strength of the integrated temperature control/alignment system. Each secondary support plate has a detection slot formed therethrough. The secondary support plates are disposed in contact with the exterior facing surfaces of the respective capillary column mounting plates in such manner that the detection slots are aligned with the detection slit and hole, respectively.

Thermoelectric plates are disposed in contact with the exterior facing surfaces of the respective secondary support plates. Each thermoelectric plate includes one or more thermoelectric conducting circuits or thermopiles functioning to regulate heat transfer with the capillary column. During typical electrophoretic operating conditions, the thermoelectric plates function to provide thermoelectric cooling for the capillary column sandwiched within the integrated temperature control/alignment system by transferring Joule heat produced within the capillary column through the respective plates of the integrated temperature control/alignment system to the ambient environment.

Controlling the direction and magnitude of the current flow through the thermoelectric conducting circuits permits thermoelectric regulation of both the direction and rate of heat transfer with the capillary column, and the ambient environment as required. The direction of heat transfer may be such as to either dissipate or augment the Joule heat generated within the capillary column, such that the temperature of the capillary column is precisely controlled. Each thermoelectric plate can include a detection passageway aligned with the respective detection slot, the detection passageway being required when the thermoelectric plate is one unitary thermopile, that is a single thermoelectric conducting circuit.

External heat sink plates are disposed in contact with respective thermoelectric plates to transfer Joule heat away from the capillary column when the system operates to provide thermoelectric cooling of the capillary column. The external heat sink plates act to transfer the thermal energy or Joule heat of the higher temperature surface of the thermoelectric plates to the external ambient environment. Heat transfer to the ambient environment may be effected by radiative, convective, and/or conductive heat transfer from the external heat sink plates. Detection apertures are formed through the external heat sink plates so as to be aligned with the detection slots or the detection passageways, depending upon the particular configuration of the thermoelectric plates.

BRIEF DESCRIPTION OF THE DRAWINGS

A more complete understanding of the present invention and the attendant advantages and features thereof will be more readily understood by reference to the following detailed description when considered in conjunction with the accompanying drawings wherein:

FIG. 1 is a schematic representation of one embodiment of a high performance capillary electrophoretic apparatus utilizing an integrated temperature control/alignment system according to the present invention;

FIG. 2 is a perspective view of a capillary column illustrating the opposed detection windows thereof;

FIG. 3 is a cross sectional view taken along line 3—3 of FIG. 1 of one embodiment of the integrated temperature control system of the present invention;

FIG. 4 is a perspective view of the capillary column mounting plates according to the present invention;

FIG. 5 is a perspective view of a secondary support plate according to the present invention;

FIG. 6 is a schematic representation of a thermopile;

FIG. 7 is a perspective view of one embodiment of a thermoelectric plate according to the present invention;

FIG. 8 is a perspective view of an alternative embodiment of the thermoelectric plate according to the present invention., FIG. 9 is a perspective view of one embodiment of a heat sink plate for use with the present invention;

DETAILED DESCRIPTION OF THE PREFERRED EMBODIMENTS

Figure 10:
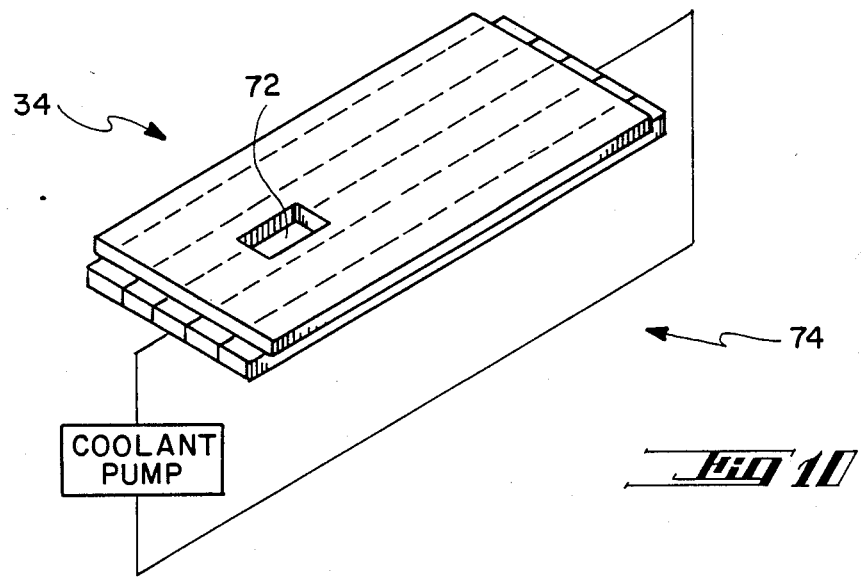
FIG. 10 is a perspective view of an alternative embodiment of a heat sink plate for use with the present invention.

Referring now to the drawings wherein like reference numerals designate corresponding or similar elements throughout the several views, there is shown generally in FIG. 1 a high performance capillary electrophoretic (HPCE) apparatus 10 according to the present invention. The basic capillary electrophoretic apparatus 10 comprises a capillary tube or column 12 having ends 14, 14 disposed in buffer solution reservoirs 16, 16.

Electrodes 18, 20 electrically connect the buffer solution reservoirs 16, 16 to apply a voltage, Vep, across the electrodes 18, 20, respectively, thereby providing the motive force for electrophoretic migration of an analyte. The capillary column 12 is mounted as a constituent of the HPCE apparatus 10 by means of an integrated temperature control/alignment system 26, as described hereinbelow in greater detail.

An on-column detection device 22, 24 is externally prepositioned with respect to the HPCE apparatus 10 for on-column detection of the electromigrating analyte. For purposes of illustration only, the on-column detection device 22, 24 is herein described as a UV radiation source 22 which focuses UV radiation to pass through the detection openings of the integrated temperature control/alignment system 26 and the detection windows of the capillary column 12 for ensuing detection by a detection means 24.

The capillary column 12 is a thin-walled, hollow tube, preferably formed of a low specific heat, non-conducting material such as fused silica. The capillary column 12 may be either "open" or "gel." Typical gels for the interior of the capillary column 12 include polyacrylamide or agarose.

The capillary column 12 typically has a length in the range of 10 cm to 100 cm, an internal diameter (I.D.) in the range of 25 microns to 200 microns, and an outer diameter (O.D.) in the range of 125 microns to 350 microns, depending upon the I.D. of the capillary column 12. Since a quartz based fused silica capillary column 12 having the above-disclosed dimensions is relatively fragile, the strength and flexibility of the capillary column 12 are generally increased by applying an external protective coating of a polymer such as polyimide to the capillary column 12.

The polyimide coating, however, would interfere with the operation of the on-column detection device 22, 24. Therefore, the coating of the capillary column 12 is typically modified to include detection "windows" which permit measurement or sensing of the electromigrating analyte during passage through the interior of the capillary column 12. As shown in FIG. 2, the polyimide coating is selectively removed at opposed locations on the capillary column 12 at the predetermined position to create first and second detection windows 13', 13'', spaced approximately 180 degrees from one another.

Alternatively, a 360 degree peripheral band of the polyimide coating may be removed at the predetermined position on the capillary column 12. One of ordinary skill in the art will appreciate that "windows" is used herein in a generic sense to refer to a modified segment or segments of the capillary column 12 at the predetermined position wherein some form of measurement/sensing means is provided access into and out of the capillary column 12 to detect the electromigrating analyte. To simplify the ensuing discussion, the on-column detection device 22, 24 is exemplarily described as a UV radiation source and UV detection means.

The irradiated volume within the capillary column 12 between the detection "windows" defines the electrophoretic detection zone. The detection radiation generated by the on-column detection device 22, 24 is focused to traverse the detection zone of the capillary column 12.

During the generation of electropherograms the ends 14, 14 of the capillary column 12 are disposed in the buffer solution reservoirs 16, 16 in such a manner as to be in fluidic contact with the buffer solution. Prior to insertion of the ends 14, 14 in the respective buffer solution reservoirs 16, 16, the interior of the capillary column 12 is filled with the gel/buffer solution and the analyte is electrophoretically injected into the appropriate end 14 thereof. The buffer solution acts as the electrically conductive medium for the electrophoretic circuit.

The electrophoretic conducting circuit for the HPCE apparatus 10 is completed by inserting the first electrode 18 in one buffer solution reservoir 16 and the second electrode 20 in the other buffer solution reservoir 16. The electrodes 18, 20 are preferably formed of a chemically inert material such as platinum to preclude a degrading reaction between the electrodes 18, 20 and the buffer solution of the reservoirs 16, 16.

Figure 11:
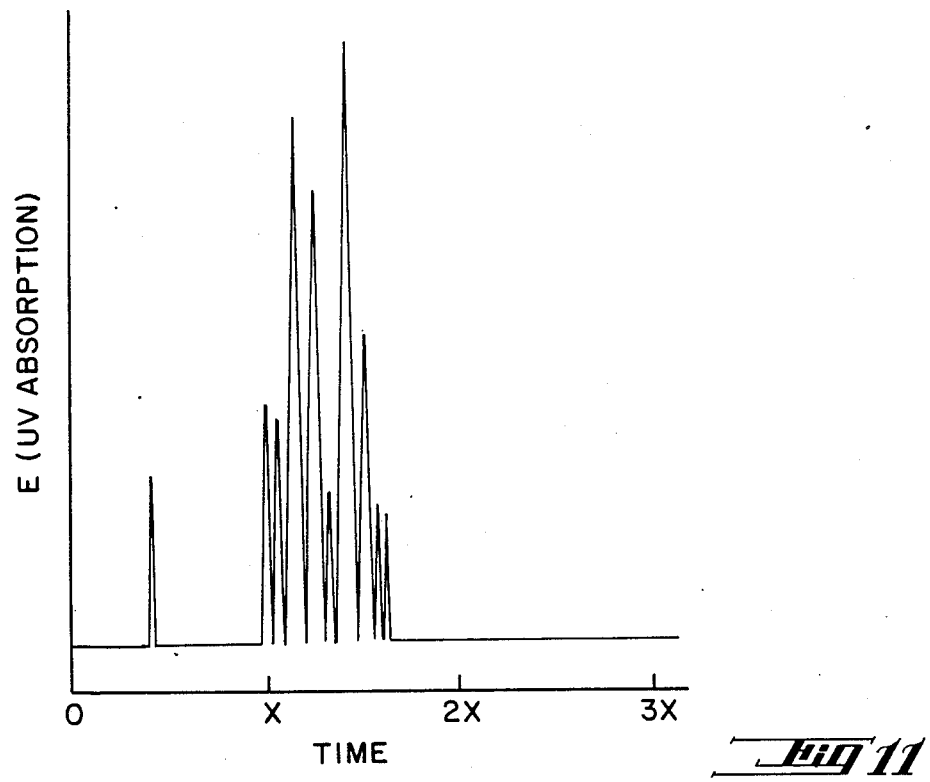
FIG. 11 is an exemplary electropherogram generated by means of an HPCE apparatus.

During electrophoresis, the voltage, Vep, is applied across the HPCE apparatus 10 to generate a current in the electrophoretic circuit. The applied voltage, $V_{ep}$, causes the electromigration of the analyte injected into the appropriate end 14 of the capillary column 12 through the capillary column 12 to the other end 14. Passage of the analyte through the capillary tube 12 past the prepositioned on-column detection device 22, 24 causes the generation of an electropherogram which is a graphical time display of the quanta of detected radiation. The passage of the electromigrating analyte through the detection zone causes the monochromatic radiation traversing the capillary column 12 to be scattered and/or absorbed. A representative example of an electropherogram derived by means of the HPCE apparatus 10 is shown in FIG. 11.

The exemplary on-column detection device 22, 24 comprises a means for generating a monochromatic beam of UV radiation 22 and focusing the beam to pass substantially orthogonally through the first detection window 13' of the capillary column 12. One such monochromatic radiation generating means 22 having utility in the HPCE apparatus 10 of the present invention is an UV deuterium lamp producing ultraviolet radiation in the 190-380 nanometer range. By means of a suitable lens/filter arrangement the monochromatic beam of ultraviolet radiation, of predetermined wavelength, is focused to radiate through the first detection window 13' substantially orthogonal thereto.

The monochromatic radiation traverses the capillary column 12 and the medium, e.g., gel, buffer solution and/or analyte, disposed between the first and second detection windows 13', 13'' and exits therefrom through the second detection window 13''. The exiting radiation is focused upon a suitable detection means 24 such as a photomultiplier which is responsive to changes in radiation intensity. When the analyte in the capillary column 12 electromigrates through the detection zone between the first and second detection windows 13', 13'' the monochromatic radiation is scattered and/or absorbed, thereby generating an electropherogram as shown in FIG. 11.

Other usable monochromatic radiation may be produced by IR and visible radiation sources. Fluorescence is another detection technique usable for on-column monitoring of the electrophoretically migrating analyte. It will be appreciated that the on-column detection technique is not limited to the generation and detection of radiation. Other detection techniques having utility for on-column detection include conductivity and electrochemical measurements/sensing. The common denominator for all on-column detection techniques is access to the capillary column in some predetermined manner.

One embodiment of the integrated temperature control/alignment system 26 for mounting the capillary column 12 as a constituent of the HPCE apparatus 10 is shown in greater detail in the end view of FIG. 3. The temperature control/alignment system 26 of FIG. 3 is a multi-layered structure consisting of a pair of capillary column mounting members or plates 28, 28 for mounting the capillary column 12 as part of the HPCE apparatus 10, a pair of secondary support plates 30, 30, a pair of thermoelectric plates 32, 32, and external heat sink plates 34, 34.

The capillary column mounting plates 28, 28 illustrated in FIG. 4 are preferably fabricated from an electrically insulating material, preferably a ceramic-type material having good dielectric characteristics and possessing a reasonable coefficient of thermal conductivity. One suitable ceramic material is alumina, $Al_2O_3$, which has a thermal conductivity of approximately 0.0723 cal/cm °C. sec. at 100 ° C. It will be appreciated, however, that the capillary column mounting plates 28, 28 may be fabricated from metallic conducting materials for some applications. Each capillary column mounting plate 28 has a lengthwise groove 36 formed in an interior facing surface thereof.

The groove 36 has a maximum width which is approximately equal to the O.D. of the capillary column 12 and a depth which is approximately equal to one half of the O.D. of the capillary column 12. The dimensioning of the grooves 36 ensures that the capillary column 12 is snugly seated or physically engaged therein, and further that when the interior facing surfaces of the capillary column mounting plates 28, 28 are disposed in contacting relationship, the capillary column 12 is locked or sandwiched therebetween in an immobile condition.

A detection slit 38 is formed through the upper capillary column mounting plate 28 in such a manner as to be substantially centered about the groove 36 thereof and a detection hole 40 is formed through the lower capillary column mounting plate 28 in such a manner as to be substantially centered about the groove 36 thereof, as shown in FIG. 4. The detection slit 38 has a length in the range of about 2 mm or less and a width in the range approximately equal to or less than the I.D. of the capillary column 12. The detection hole 40 has a diameter in the range of about 2 mm or less. When the upper and lower capillary column mounting plates 28, 28 are disposed in contacting relationship, as shown in FIG. 3, the detection slit 38 is aligned with the detection hole 40.

The detection slit 38 and the detection hole 40 are formed through the upper and lower capillary column mounting plates 28, 28 in such a manner that when the capillary column 12 is seated in the opposed grooves 36 of the capillary support strips 28, 28, the detection slit 38 can be readily aligned with the first detection window 13' and the detection hole 40 can be readily aligned with the second detection window 13". The structural configuration of the capillary column mounting plates 28, 28 thus facilitates the alignment of the capillary column 12 with respect to the prepositioned on-column detection device 22, 24, thereby ensuring the reproducibility of results as well as consistency therebetween.

With the grooved faces of the capillary column mounting plates 28, 28 secured together in a contacting relationship, the capillary column 12 is locked in the opposed grooves 36 thereof. A thermally conductive paste may be used to ensure a tight, thermally conducting pathway between the capillary column 12 and the capillary column mounting plates 28, 28.

Disposed in contact with the exterior facing surfaces of the capillary column mounting plates 28, 28 are the interior facing surfaces of the secondary support plates 30, 30, as shown in FIG. 5. The secondary support plates 30, 30 are typically fabricated as metal members or plates which provide a good thermally conductive medium between the capillary column mounting plates 28, 28 and the thermoelectric plates 32, 32 to facilitate the transfer of Joule heat between the capillary column 12 and the thermoelectric plates 32, 32.

In addition, the secondary support plates 30, 30 provide increased structural strength for the integrated temperature control/alignment system 26. Representative metals having utility in forming the secondary support plates 30, 30 for use in the present invention include copper, which has a thermal conductivity of approximately 0.9512 cal/cm °C. sec at 25 ° C., and aluminum, which has a thermal conductivity of approximately 0.5664 cal/cm °C. sec at 25 °C.

As shown in FIG. 5, a detection slot 42 is formed in each of the secondary support plates 30, 30 in such manner that when the integrated temperature control/alignment system 26 is assembled in final configuration with the capillary column 12 sandwiched therein, the detection slots 42 of the secondary support plates 30, 30 are aligned with the detection slit 38 and the detection hole 40, respectively, of the capillary column mounting plates 28, 28.

The interior facing surfaces of the thermoelectric plates 32, 32 are disposed in contact with the exterior facing surfaces of the secondary support plates 30, 30, respectively. Each thermoelectric plate 32 comprises at least one electrically conducting circuit or thermopile utilizing the Peltier effect to thermoelectrically regulate the electrophoretic operating temperature, $T_{cc}$ of the capillary column 12 by the controlling the transfer of thermal energy to or from the capillary column 12.

The Peltier effect describes a phenomenon wherein an electric current flowing through the junction between two dissimilar metals or conducting elements, i.e., a thermocouple, can absorb or generate thermal energy at the junction depending upon the direction of the current flow. The rate of heat transfer at the junction is directly proportional to the magnitude of the current flowing through the junction. The thermal energy transfer rate is thus directly controllable by regulating the magnitude of the current flowing through the thermoelectric circuit. , In addition, by controlling the direction of current flow in the thermoelectric circuit, the thermoelectric effect exerted on the capillary column 12 is regulated to provide either thermoelectric cooling or thermoelectric heating of the capillary column 12.

To simplify the disclosure, the operation of the thermoelectric plates 32, 32 will be described in terms of providing thermoelectric cooling for the capillary column 12, i.e., the thermoelectric plates 32, 32 act to transfer the Joule heat generated in the capillary column 12 to the heat sink plates 34, 34 via the capillary column mounting plates 28, 28, the secondary support plates 30, 30 and the thermoelectric plates 32, 32, since electrophoretic operations typically are concerned with the dissipation of Joule heat generated within the capillary column 12- The thermoelectric cooling provided by the thermoelectric plates 32, 32 thus effectively cools the secondary support plates 30, 30, and the capillary column mounting plates 28, 28 and concomitantly lowers the electrophoretic operating temperature, $T_{cc}$, of the capillary column 12 to a predetermined operating temperature.

By connecting a plurality of thermocouples in series to an external current source, a thermopile 50 is formed, as schematically illustrated in FIG. 6. The thermopile 50 is comprised of a first plurality of conducting elements 52 and a second plurality of conducting elements 54 joined as shown in FIG. 6 to form a first plurality of dissimilar junctions 56 and a second plurality of dissimilar junctions 58 electrically connected to a variable current source 60. Bismuth telluride is a representative compound used in forming the conducting elements of the thermopile 50, with the first and second plurality of conducting elements 52, 54 formed by doping the bismuth telluride with "p" and "n" type metals, respectively.

The first plurality of dissimilar junctions 56 are disposed in first planes 62 to form the interior facing surfaces of the first and second thermoelectric plates 32, 32 and the second plurality of dissimilar junctions 58 are disposed in second planes 64 to form the exterior facing surfaces of the first and second thermoelectric plates 32, 32. The junctions may be maintained in such a relationship permanently, as for example by fixing the thermocouples in an epoxy infrastructure of suitable electrically insulating material.

Proper selection of the magnitude and direction of the current generated by the variable current source 60 flowing in the thermopile circuit 50 maintains the first plurality of dissimilar junctions 56 at a temperature, $T_L$, while the second plurality of dissimilar junctions 58 are maintained at a temperature, $T_H$, that is, the first plurality of dissimilar junctions 56 cool down while the second plurality of dissimilar junctions 58 heat up.

The thermoelectric plates 32, 32 are configured such that during electrophoresis the temperature $T_L$ maintained at the first plurality of dissimilar junctions 56 is less than the predetermined electrophoretic operating temperature, $T_{cc}$, at which the capillary column 12 is operated during electrophoresis. This ensures that a heat transfer potential is maintained between the capillary column 12 and the interior facing surfaces of the thermoelectric plates 32, 32 such that Joule heat generated in the capillary column 12 during electrophoresis is transferred away from the capillary column 12. The value of $T_L$, and hence the rate of thermal energy transfer or the thermoelectric cooling effect of the thermoelectric plates 32, 32, is regulated by varying the output of the current source 60 such that the operating temperature, $T_{cc}$, of the capillary column 12 is precisely maintained. One or more thermopiles 50 as described hereinabove are arranged to function singly or in combination as the thermoelectric plates 32, 32 utilized in the integrated temperature control/alignment system 26 according to the present invention.

The embodiment of the thermoelectric plate 32 shown in FIG. 7 is a unitary thermopile 50, that is a single thermoelectric circuit, which has the first plurality of dissimilar junctions 56 disposed so as to form the interior facing surface 62 in contact with the exterior facing surface of the respective secondary support plate 30 while the second plurality of dissimilar junctions 58 are disposed to form the exterior facing surface 64 in contact with the interior facing surface of the respective heat sink plate 34. Since the embodiment of the thermoelectric plate 32 of FIG. 7 is a unitary thermopile 50, each thermoelectric plate 32 must be modified to include a detection passageway 66 aligned with the respective detection slot 42 of the corresponding secondary support plate 30 for on-column detection of the electrophoretically migrating analyte.

FIG. 8 illustrates another embodiment of the thermoelectric plate 32 of the present invention wherein each thermoelectric plate 32 consists of a plurality of individual thermopiles 50, four being shown in FIG. 8, which act in combination to transfer thermal energy from the secondary support plate 30 to the heat sink plate (not shown). As illustrated in FIG. 8 each thermopile 50 has its own current source 60. The individual current sources 60 may be gang controlled to regulate the temperature $T_L$. It will be appreciated that the individual thermopiles 50 of each thermoelectric plate 32 can be disposed to form, in effect, a detection passageway 66. This is accomplished by affixing the individual thermopiles 50 to the exterior facing surfaces of the corresponding secondary support plates 30, 30 so as not to overlap or obstruct the detection slots 42, 42.

One embodiment of the heat sink plate 34 of the present invention is depicted in FIG. 9. Each heat sink plate 34 of the embodiment of FIG. 9 includes a plurality of radiating fins 70 for externally dissipating the thermal energy transferred to the heat sink plate 34 by radiative and/or convective heat exchange between the radiating fins 70 and the ambient environment where the HPCE apparatus 10 is set up. The convective heat exchange of the heat sink plate 34 may be either passive or active. Operating the heat sink plate 34 for active convective heat exchange requires the utilization of any conventionally known means for forcing a greater fluid volume over the surface area of the heat sink plate 34 to increase the rate of convective heat exchange between the heat sink plate 34 and the fluid. Each heat sink plate 34 also includes a detection aperture 72 aligned with the respective detection passageway 66 of the thermoelectric plate 32 (for the embodiment disclosed by FIG. 7) or the detection slot 42 of the respective secondary support plate 30 (for the embodiment disclosed by FIG. 8).

Alternatively, as shown in FIG. 10 the heat sink plate 34 can be primarily cooled by conduction by means of a cooling system 74 which circulates a cooling fluid for heat exchange through the heat sink plate 34. Such an embodiment is effective where the capillary column 12 of the HPCE apparatus 10 is to be operated at predetermined operating temperatures $T_{cc}$ which require large quanta of Joule heat to be transferred to the ambient environment. The circulating cooling fluid ensures that the necessary heat transfer potential is maintained for effective Joule heat transfer between the thermoelectric plates 32, 32 and the heat sink plates 34, 34. This embodiment likewise includes the detection aperture 72 as described hereinabove.

The integrated temperature control/alignment system 26 described hereinabove provides an improved means for regulating heat transfer between the capillary column 12 and the ambient environment. The direction and rate of heat transfer with respect to the capillary column 12 is regulated by the thermoelectric effect provided by means of the magnitude and direction of the electric current flowing in the thermoelectric plates 32, 32. Regulation of the direction and rate of heat transfer regulates or controls the electrophoretic operating temperature, $T_{cc}$, of the capillary column 12. By utilizing the integrated temperature control/alignment system 26 to thermoelectrically cool the capillary column 12 as described in the preceding paragraphs, the HPCE apparatus 10 according to the present invention is operable at higher $V_{ep}s$, which results in the generation of higher resolution electropherograms and/or analyte separation in shorter run times. By utilizing the integrated temperature control/alignment system 26 according to the present invention, reproducible high quality results are obtainable down to electrophoretic operating temperature, $T_{cc}$, of $-20$ °C.

It is to be understood that the integrated temperature control/alignment system 26 of the present invention can also be utilized to thermoelectrically heat the capillary column 12, that is, to augment the Joule heat generated within the capillary column 12 to raise the electrophoretic operating temperature, $T_{cc}$. When the integrated temperature control/alignment system 26 is operated to thermoelectrically heat the capillary column 12, the heat sink plates 34, 34 need not be included as elements of the integrated temperature control/alignment system 26.

It will further be appreciated that the structural configuration of the integrated temperature control/alignment system 26 as described hereinabove provides thermoelectric regulation of the temperature proximal the detection zone of the capillary column 12. This likewise increases the accuracy and reproducibility of the electrophoretic separation. Moreover, the disclosed structural configuration of the integrated temperature control/alignment 26 system facilitates the proper alignment of the windows of the capillary column 12 with respect to the prepositioned on-column detection device 22, 24, i.e., in the detection zone.

A variety of modifications and variations of the present invention are possible in light of the above teachings. For example, another embodiment of the integrated temperature control/alignment system comprises only the capillary column mounting plates and the thermoelectric plates as described hereinabove. Another embodiment of the integrated temperature control/alignment system comprises only the thermoelectric plates, the interior facing surfaces of each thermoelectric plate having formed therein grooves and a detection slit and a detection hole, respectively, as described hereinabove for seating and locking the capillary column in alignment with the prepositioned on-column detection device.

Although the embodiments of the integrated temperature control/alignment system have been described hereinabove in terms of a plate configuration, it is to be understood that the present invention is not to be limited by the terminology "plate". The integrated temperature control/alignment system can also be formed as series of individual concentric tubes, as functionally described hereinabove, coaxially disposed about the capillary column. It will be appreciated that for this embodiment no groove is necessary in the capillary column support tube in that the configuration of the tube itself performs the seating and locking function. It is therefore to be understood that within the scope of the appended claims, the present invention may be practiced otherwise than as specifically described hereinabove.

What is claimed as new and desired to be secured by Letters Patent of the United States is:

1. An integrated temperature control/alignment system disposed in an ambient environment for use with a high performance electrophoretic apparatus including a capillary column and an externally prepositioned on-column detection device, comprising:

means for thermoelectrically regulating heat transfer between the capillary column and the ambient environment to maintain the capillary column at a predetermined electrophoretic operating temperature, said thermoelectric regulating means including means for mounting the capillary column as part of the electrophoretic apparatus, said mounting means being formed from an electrical insulating material having a coefficient of thermal conductivity to provide efficient heat transfer between the capillary column and said mounting means sufficient to maintain the capillary column at said predetermined electrophoretic operating temperature, said mounting means including means for aligning the capillary column in a predetermined position to the externally prepositioned on-column detection device within said integrated temperature control/alignment system as part of the electrophoretic apparatus for on-column detection, and means for physically engaging the capillary column to lock the capillary column in said predetermined position within said integrated temperature control/alignment system.

2. The integrated temperature control/alignment system of claim 1 wherein said capillary column mounting means comprises at least one thermoelectric member having an interior facing surface and an exterior facing surface, said at least one thermoelectric member having aligned detection openings formed therethrough from said interior facing surface to said exterior facing surface for aligning the capillary column in said predetermined position to the externally prepositioned on-column detection device for on-column detection, said aligned detection openings comprising said capillary column alignment means, and wherein said interior facing surface of said at least one thermoelectric member comprises said means for physically engaging the capillary column to lock the capillary column within said integrated temperature control/alignment system in said predetermined position, and wherein said at least one thermoelectric member comprises at least one thermopile thermoelectrically regulating said heat transfer between the capillary column and the ambient environment to maintain the capillary column at said predetermined electrophoretic operating temperature.

3. An integrated temperature control/alignment system disposed in an ambient environment for use with a high performance electrophoretic apparatus including a capillary column and an externally prepositioned on-column detection device, comprising:

means for mounting the capillary column as part of the electrophoretic apparatus, said mounting means being formed from an electrical insulating material having a coefficient of thermal conductivity to efficient provide heat transfer between the capillary column and said mounting means sufficient to maintain the capillary column at a predetermined electrophoretic operating temperature, said mounting means further comprising means for aligning the capillary column in a predetermined position to the externally prepositioned on-column detection device within said integrated temperature control/alignment system as part of the electrophoretic apparatus, and means for physically engaging the capillary column to lock the capillary column in said predetermined position within said integrated temperature control/alignment system; and means for thermoelectrically regulating heat transfer between the capillary column and the ambient environment to maintain the capillary column at said predetermined electrophoretic operating temperature.

4. The integrated temperature control/alignment system of claim 3 wherein said thermoelectric regulating means provides thermoelectric cooling for the capillary column to transfer Joule heat from the capillary column to the ambient environment to maintain the capillary column at said predetermined electrophoretic operating temperature.

5. The integrated temperature control/alignment system of claim 3 wherein said thermoelectric regulating means provides thermoelectric heating for the capillary column to transfer heat to the capillary column to maintain the capillary column at said predetermined electrophoretic operating temperature.

6. The integrated temperature control/alignment system of claim 3 wherein said capillary column mounting means comprises at least one capillary column mounting member having interior and exterior facing surfaces, said at least one capillary column mounting member having aligned detection openings formed therethrough from said interior facing surface to said exterior facing surface for aligning the capillary column in said predetermined position for on-column detection, said aligned detection openings comprising said capillary column alignment means, and wherein said interior facing surface of said at least one capillary column mounting member comprises said means for physically engaging the capillary column to lock the capillary column within said integrated temperature control/alignment system in said predetermined position to the externally prepositioned on-column detection device, and wherein said thermoelectric regulating means acts upon said exterior facing surface of said at least one capillary column mounting member to regulate thermoelectrically said heat transfer between the capillary column and the ambient environment to maintain the capillary column at said predetermined electrophoretic operating temperature.

7. The integrated temperature control/alignment system of claim 6 wherein said thermoelectric regulating means comprises at least one thermoelectric member having interior and exterior facing surfaces and detection passageways formed therethrough in alignment with said aligned detection openings of said at least one capillary column mounting member to align the capillary column in said predetermined position to the externally prepositioned on-column detection device within said integrated temperature control/alignment system for on-column detection, and wherein said interior facing surface of said at least one thermoelectric member is disposed adjacent said exterior facing surface of said at least one capillary column mounting member to regulate thermoelectrically said heat transfer between the capillary column and the ambient environment to maintain the capillary column at said predetermined electrophoretic operating temperature.

8. The integrated temperature control/alignment system of claim 7 wherein said at least one capillary column mounting member comprises first and second capillary column mounting plates having a groove formed in said interior facing surface of each said first and second capillary column mounting plates, said grooves comprising said means for physically engaging the capillary column to lock the capillary column within said integrated temperature control/alignment system in said predetermined position to the externally prepositioned on-column detection device for on-column detection, and wherein said aligned detection openings are formed through said first and second capillary column mounting plates from said interior facing surfaces to said exterior facing surfaces substantially centered about said grooves for alignment of the capillary column in said predetermined position to the externally prepositioned on-column detection device for on-column detection, and wherein said aligned detection opening of said first capillary column mounting plate is a detection slit and said aligned detection opening of said second capillary column mounting plate is a detection hole, and wherein said at least one thermoelectric member comprises first and second thermoelectric plates having said interior facing surfaces disposed adjacent respective exterior facing surfaces of said first and second capillary column mounting plates and said exterior facing surfaces exposed to the ambient environment, and wherein said detection passageways are formed through said first and second thermoelectric plates from said interior facing surfaces to said exterior facing surfaces in alignment with said aligned detection openings of said first and second capillary column mounting plates with said first and second thermoelectric members disposed adjacent said first and second capillary column mounting plates, respectively, and wherein said first and second thermoelectric plates thermoelectrically regulate said heat transfer between the capillary column locked in said grooves of said first and second capillary column mounting plates and the ambient environment to maintain the capillary column at said predetermined electrophoretic operating temperature.

9. The integrated temperature control/alignment system of claim 7 wherein said at least one thermoelectric member comprises at least one thermopile having a first plurality of dissimilar junctions and a second plurality of dissimilar junctions disposed adjacent said interior and exterior facing surfaces, respectively, to regulate thermoelectrically said heat transfer between the capillary column and the ambient environment to maintain the capillary column at said predetermined electrophoretic operating temperature, and current generator means for regulating current flow direction and magnitude in said at least one thermopile wherein current flow in a first direction maintains said first plurality of dissimilar junctions at a first temperature and said second plurality of junctions at a second temperature to provide thermoelectric cooling of the capillary column and wherein current flow in a second direction maintains said first plurality of dissimilar junctions at a third temperature and said second plurality of junctions at a fourth temperature to provide thermoelectric heating of the capillary column.

10. The integrated temperature control/alignment system of claim 7 further comprising at least one secondary support member having interior and exterior facing surfaces and detection slots formed therethrough in alignment with said aligned detection openings of said at least one capillary column mounting member and said detection passageways of said at least one thermoelectric member with said at least one secondary support member disposed intermediate said at least one capillary column mounting member and said at least one thermoelectric member to align the capillary column in said predetermined position to the externally prepositioned on-column detection device within said integrated temperature control/alignment system for on-column detection, and wherein said thermoelectric regulating means coacts with said at least one secondary support member to regulate thermoelectrically said heat transfer between the capillary column and the ambient environment to maintain the capillary column at said predetermined electrophoretic operating temperature.

11. The integrated temperature control/alignment system of claim 10 further comprising
at least one heat sink member having interior and exterior facing surfaces and detection apertures formed therethrough, and wherein said detection apertures are aligned with said detection passageways of said at least one thermoelectric member with said at least one heat sink member disposed adjacent said exterior facing surface of said at least one thermoelectric member to align the capillary column in said predetermined position to the externally prepositioned on-column detection device within said integrated temperature control/alignment system for on-column detection, and wherein said at least one heat sink member coacts with said at least one thermoelectric member to transfer thermal energy between said at least one thermoelectric member and the ambient environment.

12. The integrated temperature control/alignment system of claim 11 further comprising
means for forcing a fluid over said exterior facing surface of said at least one heat sink member for convective cooling thereof to facilitate transfer of said thermal energy between said at least one heat sink member and the ambient environment.

13. The integrated temperature control system of claim 11 wherein said at least one heat sink member further includes means for circulating a cooling fluid proximal said exterior facing surface of said at least one heat sink member for conductive cooling thereof to facilitate transfer of said thermal energy between said at least one heat sink member and the ambient environment.

14. The integrated temperature control/alignment system of claim 8 further comprising
first and second secondary support plates having interior and exterior facing surfaces and detection slots formed through said first and second secondary support plates between said interior and exterior facing surfaces thereof, and wherein said first and second secondary support plates are disposed intermediate said first and second capillary column mounting plates and said first and second thermoelectric plates, respectively, with said detection slots aligned with said detection slit and said detection hole of said first and second capillary column mounting plates, respectively, and said detection passageways of said first and second thermoelectric plates to align the capillary column in said predetermined position to the externally prepositioned on-column detection device within said integrated temperature control/alignment system for on-column detection, and wherein said first and second thermoelectric plates coact with said first and second secondary support plates, respectively, to regulate thermoelectrically said heat transfer between the capillary column locked in said grooves of said first and second capillary column mounting plates and the ambient environment to maintain the capillary column at said predetermined electrophoretic operating temperature.

15. The integrated temperature control system of claim 14 further comprising
at least one heat sink plate having an interior facing surface, an exterior facing surface and a detection apertures formed therethrough between said interior facing surface and said exterior facing surface, and wherein said detection aperture is aligned with said detection passageway of one of said first and second thermoelectric plates with said at least one heat sink plate disposed adjacent said exterior facing surface of said one of said first and second thermoelectric plates to align the capillary column in said predetermined position to the externally prepositioned on-column detection device within said integrated temperature control/alignment system for on-column detection, and wherein said one of said first and second thermoelectric plates coacts with said at least one heat sink plate to regulate thermoelectrically said heat transfer between the capillary column and the ambient environment by transferring thermal energy between said at least one heat sink plate and the ambient environment to maintain the capillary column at said predetermined electrophoretic operating temperature.

16. An integrated temperature control/alignment system for use with a high performance electrophoretic apparatus situated in an ambient environment, the electrophoretic apparatus including a capillary column having opposed detection windows and an externally prepositioned on-column detection means for measuring an analyte electrophoretically migrating through the capillary column, comprising:
at least one capillary column mounting member for mounting the capillary column in a predetermined position with respect to the externally prepositioned on-column detection means for measuring the analyte electrophoretically migrating through the capillary column, said at least one capillary column mounting member being formed from an electrical insulating material having a coefficient of thermal conductivity to provide efficient heat transfer between the capillary column and said at least one capillary column mounting member sufficient to maintain the capillary column at a predetermined electrophoretic operating temperature, said at least one capillary column mounting member having interior and exterior facing surfaces and aligned detection openings formed therethrough from said interior facing surface to said exterior facing surface in alignment with the opposed detection windows of the capillary column, said interior facing surface further including means for physically engaging the capillary column to lock the capillary column within said integrated temperature control/alignment system in said predetermined position with respect to the externally prepositioned on-column detection device;

at least one secondary support member having interior and exterior facing surfaces, said interior facing surface disposed in contact with said exterior facing surface of said at least one capillary column mounting member, said at least one secondary support member including detection slots formed therethrough from said interior facing surface to said exterior facing surface in alignment with the opposed detection windows of the capillary column;

at least one thermoelectric member having interior and exterior facing surfaces, said interior facing surface disposed in contact with said exterior facing surface of said at least one secondary support member, said at least one thermoelectric member including detection passageways formed therethrough from said interior facing surface to said exterior facing surface in alignment with said detection slots of said at least one secondary support member; and current generator means for regulating current flow magnitude and direction through said at least one thermoelectric member;

wherein regulation of said current flow magnitude and direction through said at least one thermoelectric member thermoelectrically regulates heat transfer between the capillary column and the ambient environment via said at least one capillary column mounting member, said at least one secondary support member and said at least one thermoelectric member to maintain the capillary column at said predetermined electrophoretic operating temperature.

17. The integrated temperature control system of claim 16 further comprising at least one heat sink member having interior and exterior facing surfaces, said interior facing surface of said at least one heat sink member disposed in contact with said exterior facing surface of said at least one thermoelectric member, said at least one heat sink member including detection apertures formed therethrough from said interior facing surface to said exterior facing surface in alignment with said detection passageways of said at least one thermoelectric member, and wherein said at least one heat sink member coacts with said at least one thermoelectric member to transfer thermal energy between said at least one thermoelectric member and the ambient environment.

18. The integrated temperature control system of claim 17 wherein said at least one thermoelectric member thermoelectrically regulates heat transfer between the capillary column and the ambient environment to provide thermoelectric cooling of the capillary column to said predetermined electrophoretic operating temperature.

19. The integrated temperature control system of claim 16 wherein said at least one thermoelectric member thermoelectrically regulates heat transfer between the capillary column and said at least one thermoelectric member to provide thermoelectric heating of the capillary column to said predetermined electrophoretic operating temperature.

* * * * *

UNITED STATES PATENT AND TRADEMARK OFFICE
CERTIFICATE OF CORRECTION

PATENT NO. : 4,898,658
DATED : February 6, 1990
INVENTOR(S) : Barry L. Karger et al It is certified that error appears in the above-indentified patent and that said Letters Patent is hereby corrected as shown below:

Column 2, line 17, "t" should read --to--.

Column 8, line 55, "circuit.," should read --circuit.--.

Column 9, line 3, "12-" should read --12.--.

Signed and Sealed this

First Day of November, 1994

Attest:

BRUCE LEHMAN

*Attesting Officer*         Commissioner of Patents and Trademarks